(12) United States Patent
Gaida

(10) Patent No.: US 7,940,455 B2
(45) Date of Patent: May 10, 2011

(54) OPHTHALMIC SURGICAL MICROSCOPE SYSTEM

(75) Inventor: Gerhard Gaida, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 342 days.

(21) Appl. No.: 11/905,198

(22) Filed: Sep. 28, 2007

(65) Prior Publication Data

US 2008/0084540 A1    Apr. 10, 2008

(30) Foreign Application Priority Data

Oct. 7, 2006 (DE) .................. 10 2006 047 459

(51) Int. Cl.
*G02B 21/32* (2006.01)
(52) U.S. Cl. .................. 359/379; 359/381; 359/384
(58) Field of Classification Search .................. 359/379, 359/381–384
See application file for complete search history.

(56) References Cited

U.S. PATENT DOCUMENTS

| | | | |
|---|---|---|---|
| 6,212,006 B1 | 4/2001 | Reiner | |
| 6,598,972 B2 | 7/2003 | Strahle | |
| 6,937,390 B2 | 8/2005 | Akiyama et al. | |
| 6,943,942 B2 | 9/2005 | Horiguchi et al. | |
| 7,085,046 B2 | 8/2006 | Horiguchi et al. | |
| 7,092,152 B2 | 8/2006 | Kirchhuebel | |
| 2002/0118448 A1 | 8/2002 | Kirchhuebel et al. | |
| 2002/0191280 A1 | 12/2002 | Horiguchi et al. | |
| 2004/0184142 A1* | 9/2004 | Akiyama et al. | 359/381 |
| 2005/0012991 A1 | 1/2005 | Sander | |

OTHER PUBLICATIONS

Expanded European Search Report (Translation into English).

* cited by examiner

*Primary Examiner* — Joshua L Pritchett
(74) *Attorney, Agent, or Firm* — Walter Ottesen

(57) ABSTRACT

An ophthalmic surgical microscope system (100) includes a surgical microscope (101). The surgical microscope (101) is accommodated on a carrier unit (109) so as to be adjustable in elevation in order to be able to adjust a work distance (124) between the surgical microscope (101) and a patient eye (120). A first drive (112) is provided for adjusting the elevation of the surgical microscope (101). The ophthalmic surgical microscope system (100) includes an ophthalmic ancillary module (114) having an adjustable ophthalmic magnifier lens (116). The work distance (125) between the ophthalmic magnifier lens (116) and the patient eye (120) can be adjusted with a second drive (117). A drive coupling (123) is provided which couples the first drive for adjusting elevation of the surgical microscope (101) to the second drive (117) for adjusting the ophthalmic magnifier lens (116).

11 Claims, 6 Drawing Sheets

OPHTHALMIC SURGICAL MICROSCOPE SYSTEM

CROSS REFERENCE TO RELATED APPLICATION

This application claims priority of German patent application no. 10 2006 047 459.7, filed Oct. 7, 2006, the entire content of which is incorporated herein by reference.

FIELD OF THE INVENTION

The invention relates to an ophthalmic surgical microscope system including: a surgical microscope; a carrier unit wherein the surgical microscope is accommodated so as to be adjustable in elevation; a first drive for adjusting the surgical microscope in elevation; an ophthalmic ancillary module which includes an adjustable ophthalmic magnifier system; and, a second drive for adjusting the ophthalmic magnifier system. The surgical microscope is adjustable in elevation in order to be able to adjust a working distance between the surgical microscope and the eye of the patient. The adjustable ophthalmic magnifier system is provided in order to be able to adjust a working distance between the ophthalmic magnifier lens and the eye of the patient.

BACKGROUND OF THE INVENTION

An ophthalmic surgical microscope system of the kind referred to above is disclosed in German utility model registration 202 15 635 U1. There, a surgical microscope is described which is accommodated in a carriage unit on a stand so as to be adjustable in elevation. For focusing, the surgical microscope can be moved up and down in the carriage unit via a drive unit in the form of an adjusting knob. An ophthalmic ancillary module is mounted in front of the microscope main objective system of the surgical microscope. The ancillary module can be pivoted into and out of the viewing beam paths. The ophthalmic ancillary module is mounted on the surgical microscope. The ophthalmic ancillary module carries an ophthalmic magnifier lens which is adjustable in elevation. A drive is provided for adjusting the ophthalmic magnifier lens and this drive includes a threaded spindle with a drive motor. The ophthalmic ancillary module is pivoted into the viewing beam paths of the surgical microscope in order to adjust the ophthalmic surgical microscope system for the examination of the ocular fundus of the eye of a patient. The surgical microscope and the ophthalmic magnifier lens are then moved until a sharp image of the ocular fundus can be seen in the binocular tube of the surgical microscope.

The Topcon Company markets an ophthalmic surgical microscope system under the product designation OMS 800 OFFISS and this ophthalmic surgical microscope system includes a surgical microscope having an ophthalmic ancillary module. The surgical microscope is accommodated on a stand unit so as to be adjustable in elevation. The ophthalmic ancillary module is mounted on this stand unit separately from the surgical microscope. The ophthalmic ancillary module includes an ophthalmic magnifier lens which can be pivoted into and out of viewing beam paths in front of the main objective system of the surgical microscope. The separate accommodation of the surgical microscope and the ophthalmic ancillary module on the stand unit permits the focusing of the surgical microscope in that the surgical microscope is moved up or down without, at the same time, changing the position of the ophthalmic magnifier lens.

SUMMARY OF THE INVENTION

It is an object of the invention to provide an ophthalmic surgical microscope system which makes it possible for an opthalmologist to adjust a surgical microscope with an ophthalmic ancillary module with a single operator-controlled unit so that the ocular fundus of the eye of the patient can be viewed sharply, with good contrast and with high light intensity.

The ophthalmic surgical microscope system of the invention defines viewing beam paths for viewing the eye of a patient. The ophthalmic surgical microscope system includes: a surgical microscope; a carrier unit for accommodating the surgical microscope therein so as to be adjustable in elevation to adjust a first distance between the surgical microscope and the eye of the patient; a first drive for adjusting the surgical microscope in elevation; an ophthalmic ancillary module including an adjustable ophthalmic magnifier lens displaceable for adjusting a second distance between the ophthalmic magnifier lens and the surgical microscope; a second drive for adjusting the ophthalmic magnifier lens; and, a drive coupling for coupling the first drive to the second drive.

In this way, an opthalmologist can adjust and focus the ophthalmic surgical microscope system rapidly and comfortably for an examination of the ocular fundus.

According to another feature of the invention, the drive coupling for the first drive for adjusting the surgical microscope in elevation is coupled in such a manner to the second drive for the adjustment of the ophthalmic magnifier lens system that the surgical microscope and the ophthalmic magnifier lens system are moved in opposite directions when the drive is activated. In this way, a constant distance of the ophthalmic magnifier lens system from the examined eye of the patient is ensured during adjustment of the system. Preferably, the drive coupling of the first drive for adjusting the surgical microscope in elevation and the second drive for adjusting the ophthalmic magnifier lens system is so configured that the surgical microscope and the ophthalmic magnifier lens system are moved at approximately the same speed.

According to another feature of the invention, the drive coupling couples the first drive for adjusting the surgical microscope in elevation to the second drive for adjusting the ophthalmic magnifier lens system in such a manner that the apparatus pupil of the system of surgical microscope and ophthalmic magnifier lens system is stationary in space. In the surgical microscope, the largest possible image field of the ocular fundus results in that the apparatus pupil is placed into the pupil of the eye of the patient. In this way, the ophthalmic surgical microscope system can be fixed to the ocular fundus without vignetting of the image field occurring in the system.

According to another feature of the invention, the first drive is configured as a motorized drive. This enables the opthalmologist to comfortably adjust the working distance of the surgical microscope.

According to still another feature of the invention, the second drive is configured as a motorized drive. In this way, especially a foot-controlled movement of the ophthalmic magnifier lens is made possible.

In another feature of the invention, the coupling is configured as an electronic coupling. This makes it possible to control the movement of the ophthalmic magnifier lens in any desired dependency upon the position of the surgical microscope without significant manufacturing complexity. In this way, especially nonlinear control functions can be realized in a simple manner.

According to another feature of the invention, the ophthalmic ancillary module includes a reducing lens system. This ensures that the ophthalmic surgical microscope system is automatically set sharply to the cornea of the examined patient eye when pivoting the ophthalmic ancillary module out of the viewing beam path.

According to still another feature of the invention, a switchable system for beam transposition and image reversion is provided in the ophthalmic surgical microscope system. This ensures that the ocular fundus of the patient eye can be made visible erect in the surgical microscope.

According to another feature of the invention, the ophthalmic ancillary module can be pivoted into and out of the viewing beam paths of the surgical microscope. This makes it possible for a viewing person to be able to alternately view the anterior section and the ocular fundus of the patient eye in rapid sequence.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
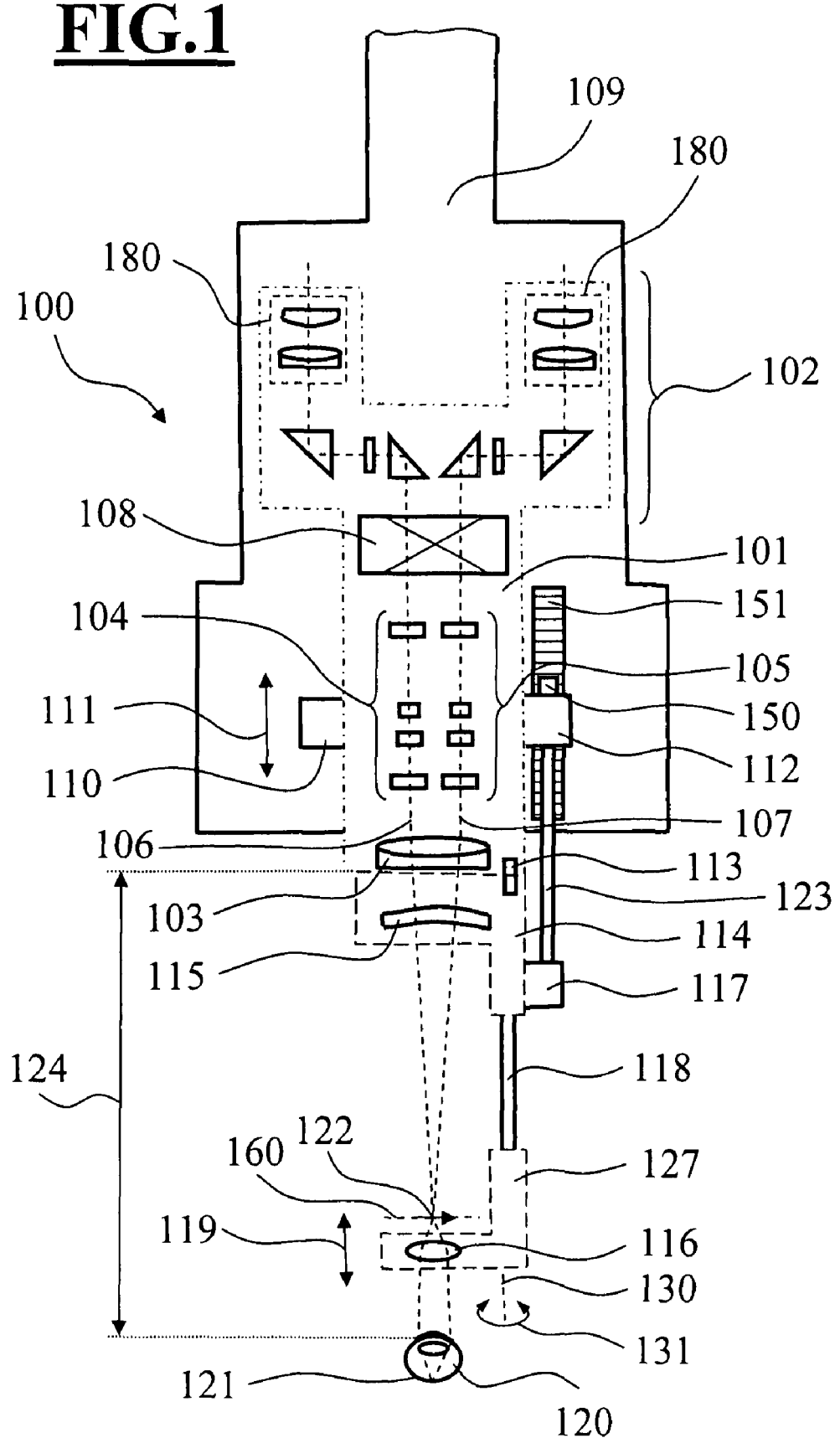
FIG. 1 is a schematic of a first ophthalmic surgical microscope system having an ophthalmic ancillary module pivoted into the viewing beam paths.

The ophthalmic surgical microscope system 100 in FIG. 1 includes a surgical microscope 101 which is configured as a stereo microscope. The surgical microscope 101 has a viewing tube 102 with an ocular 180 and a main objective system 103. The surgical microscope includes a pancratic magnification system (104, 105) for left and right binocular viewing beam paths (106, 107), respectively. A switchable system 108 for beam transposition and image reversion is mounted between the pancratic magnification system 104 and the viewing tube 102.

The surgical microscope 101 is accommodated on a carrier unit 109. It can be moved up and down on the carrier unit with a focusing unit 110 corresponding to the double arrow 111. In this way, the work distance 124 between the microscope main objective system 103 and a patient eye 120 being examined can be adjusted. In this way, the surgical microscope is focused on an object region which is to be examined.

A motorized drive 112 is assigned to the focusing unit 110. The motorized drive 112 is connected to a toothed wheel 150 which meshes in a toothed rack 151 on the carrier unit 109.

The ophthalmic surgical microscope system 100 further includes an ophthalmic ancillary module 114. The ophthalmic ancillary module is connected to the surgical microscope 101 with a pivot joint 113.

The ophthalmic ancillary module 114 includes a reducing lens 115 and an ophthalmic magnifier lens 116. The ophthalmic magnifier lens 116 is accommodated in an ophthalmic magnifier lens holder 127. The ophthalmic magnifier lens holder 127 can be moved up and down above a patient eye 120 being examined in correspondence to the double arrow 119 utilizing a drive 117 which acts on a worm gear 118. The drive 112 for adjusting the surgical microscope 101 and the drive 117 for moving the ophthalmic magnifier lens 116 coact via a coupling 123. This coupling 123 is configured as a mechanical coupling in the ophthalmic surgical microscope system 100.

Because of the refractive power of the lens 140 in a patient eye, it is necessary for the examination of the ocular fundus 121 of the patient eye 120 with a surgical microscope 101 to image the ocular fundus 121 into an intermediate image plane 160 on which the viewing beam paths (106, 107) of the surgical microscope are focused. This is the function of the ophthalmic magnifier lens 116. The ophthalmic magnifier lens generates a laterally reversed intermediate image 122 of the ocular fundus 121 of the patient eye 120 in the intermediate image plane 160. In order to be able to sharply view this intermediate image 122, the focus plane of the viewing beam paths (106, 107) of the surgical microscope 101 must be coincident with the intermediate image plane 160.

When the ophthalmic ancillary module 114 is pivoted into the viewing beam paths (106, 107) of the ophthalmic surgical microscope system 100, a switchable system for beam transposition and image reversion 108 in the surgical microscope 101 ensures that an erect image of the ocular fundus 121 of the patient eye 120 can be viewed in the viewing tube 102 of the surgical microscope 101.

The reducing lens 115 in the ophthalmic ancillary module 114 amplifies the refractive force of the main objective system 103 of the surgical microscope 101. The reducing lens 115 effects a shift of the focus plane of the viewing beam paths (106, 107) of the surgical microscope 101 toward the main objective system 103 of the surgical microscope 101.

The pivot joint 113 permits the ophthalmic ancillary module 114 to be pivoted into and out of the viewing beam paths (106, 107) about the axis 130 in correspondence to the double arrow 131. The refractive force and the arrangement of the reducing lens 115 in the ophthalmic ancillary module 114 are so selected that, when the ophthalmic ancillary module 114 is pivoted out of the viewing beam paths (106, 107), their focus plane is shifted by approximately 2.5 cm in the direction of the patient eye 120 being investigated. With the ophthalmic ancillary module 114 pivoted out, this permits the lens 140 of the patient eye 120 to be seen sharply with the surgical microscope system 100 without having to refocus the surgical microscope 101.

Figure 2:
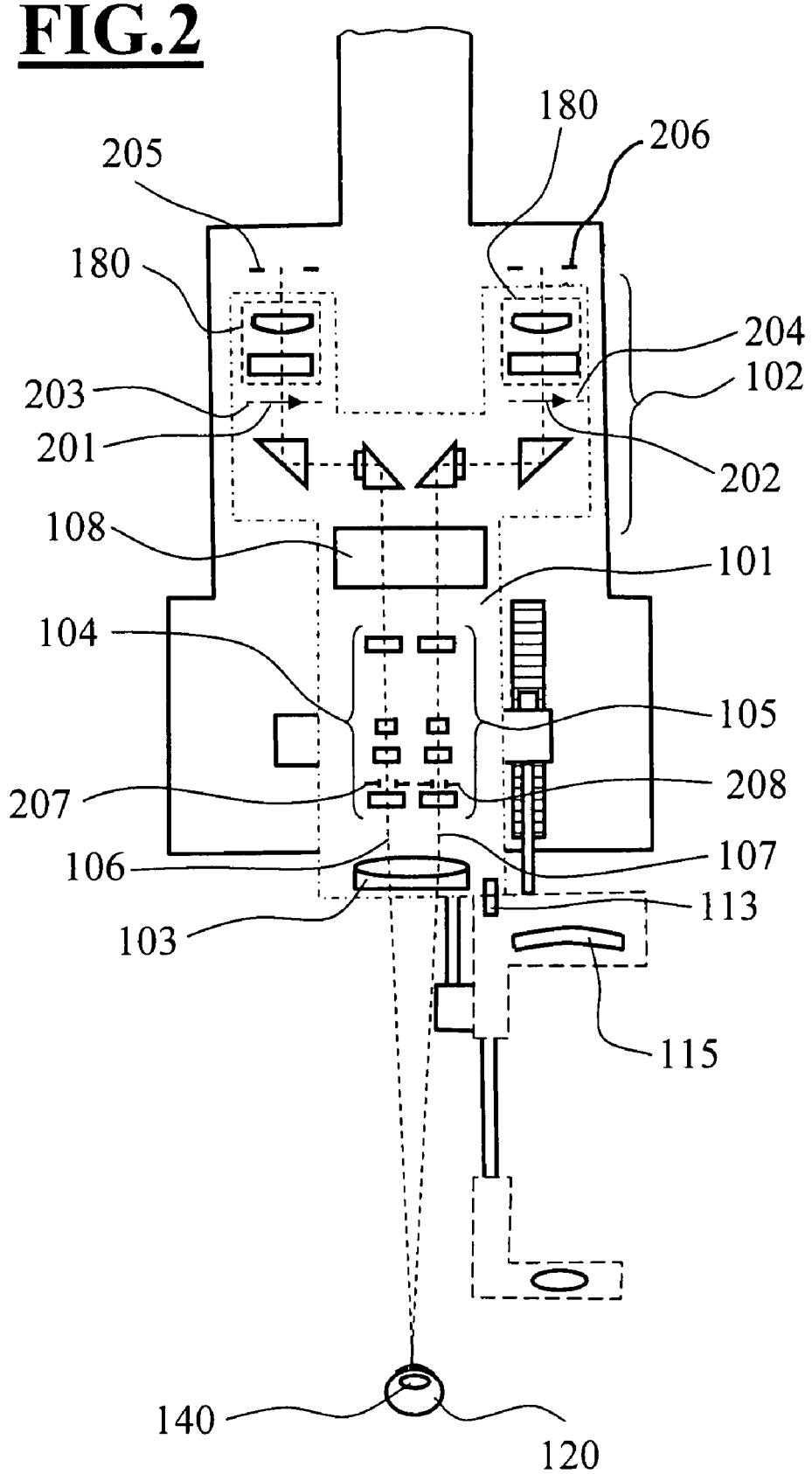
FIG. 2 shows the first embodiment of the ophthalmic surgical microscope wherein the ophthalmic ancillary module is pivoted out of the viewing beam paths.

FIG. 2 shows the ophthalmic surgical microscope system 100 with the same reference numerals being used as in FIG. 1. FIG. 2 shows the ophthalmic surgical microscope system 100 with an ophthalmic ancillary module 114 pivoted out of the viewing beam paths. Here, the system for beam transposition and image reversion 108 is switched out. In this way, the anterior eye section 140 of the patient eye 120 can be shown erect.

With the main objective system 103 and the pancratic magnification system (104, 105) in the left and right viewing beam paths (106, 107), the surgical microscope 101 generates respective intermediate images (201, 202) of the object which can be viewed with the aid of the oculars 180.

The light entering into the surgical microscope 101 from the object is delimited by the apparatus pupils (207, 208) which lie in the region of the pancratic magnification systems (104, 105). The apparatus pupils (207, 208) are imaged into the exit pupils (205, 206) via the tube 102 and the oculars 180. The positions of the exit pupils (205, 206) in the surgical microscope 101 are adapted to the typical head posture which a person assumes when viewing in the binocular tube 102. The position and the size of the apparatus pupils (207, 208) and the position and size of the exit pupils (205, 206) are coupled via a geometric imaging which is fixed by the optical elements in the surgical microscope. The exit pupils (205, 206) are an image of the apparatus pupils (207, 208) effected by the lenses in the surgical microscope.

Figure 3:
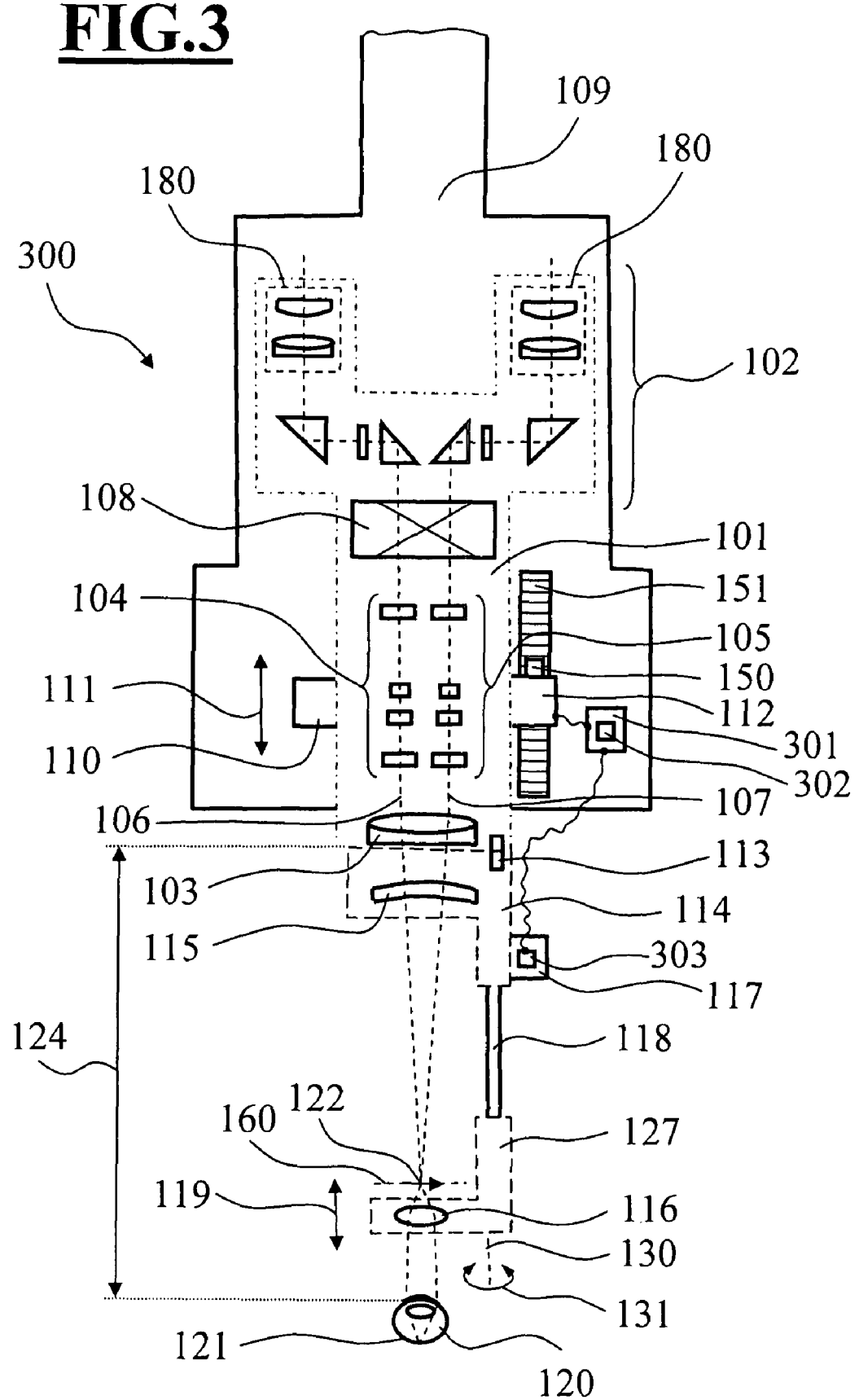
FIG. 3 is a schematic of a second ophthalmic surgical microscope system.

FIG. 3 shows an ophthalmic surgical microscope system 300 having a configuration which essentially corresponds to that of the ophthalmic surgical microscope system 100 of FIG. 1.

Component assemblies in the ophthalmic surgical microscope system 100 of FIG. 1 and the ophthalmic surgical microscope system 300 of FIG. 3 are provided with like reference numerals. In contrast to the ophthalmic surgical microscope system 100 of FIG. 1, in the ophthalmic surgical microscope system 300, there is no mechanical coupling provided but rather an electrical coupling 301 to couple the drive of the surgical microscope 101 and the drive of the ophthalmic ancillary module 114. The coupling 301 includes a control apparatus 302 which is supplied with signals of the motorized drive 112 of the focusing unit 110. These signals are processed in the control apparatus 302 in order to output a motor control signal to an electric motor 303 which is integrated into the ophthalmic ancillary module 114. This electric motor 303 acts on the drive 117 of the ophthalmic magnifier lens holder 127 in order to move the latter above the patient eye 120 in correspondence to the double arrow 119.

Figure 4:
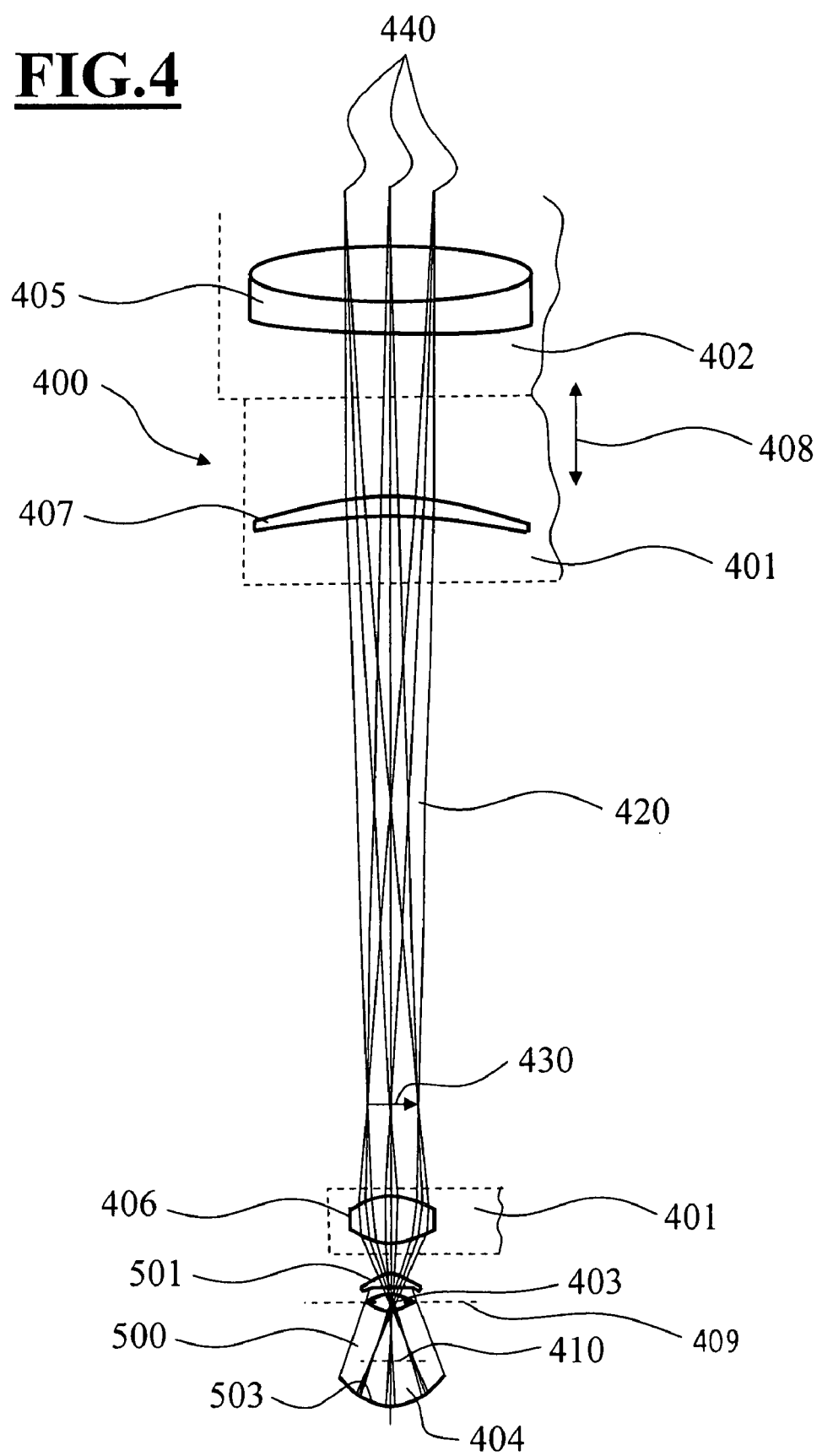
FIG. 4 is a schematic of a section of the first and second ophthalmic surgical microscope systems.

FIG. 4 shows a section 400 of the ophthalmic surgical microscope system 100 of FIG. 1 and of the ophthalmic surgical microscope system 300 of FIG. 3. The ophthalmic ancillary module 401 is pivoted into the viewing beam paths of surgical microscope 402. In this way, the apparatus pupils (207, 208) of FIG. 2 are imaged into a new apparatus pupil 403. The apparatus pupil 403 is adapted to the pupil of the patient eye 500 being examined, that is, the position of the apparatus pupil 403 corresponds to the position of the pupil of the patient eye 500. The apparatus pupil 403 lies in the pupil of the patient eye 500.

To adjust the ophthalmic surgical microscope system 100 of FIG. 1 for the examination of the ocular fundus 503 of a patient eye, a first step is to bring the apparatus pupil 403 into coincidence with the pupil of the patient eye 500 utilizing known adjustments of the reducing lens 407, ophthalmic magnification lens 406 with respect to the main objective system 405 of the surgical microscope 402 by raising and lowering the surgical microscope 402 in correspondence to the double arrow 408. This corresponds to a fixed distance of the ophthalmic magnifier lens 406 from the cornea 501 of the patient eye 500 because the distance of the pupil plane 409 of a patient eye 500 from the apex of the cornea 501 amounts to approximately 2 mm. The fixed distance of the ophthalmic magnifier lens 406 from the cornea 501 is pregiven by the adjustment of the system. The adjustment of the ophthalmic surgical microscope system shown in FIG. 4 still does not permit sharp imaging of the ocular fundus of the patient eye 500. The system is focused on an object plane 410 which lies in the middle in the vitreous body 404 of the patient eye 500. FIG. 4 shows a section of the imaging light rays 420 from one of the two binocular viewing beam paths in the ophthalmic surgical microscope system 100 of FIG. 1. The light rays pass through the ophthalmic magnifier lens 406 over the entire cross section thereof and effect an intermediate image 430 between ophthalmic magnifier lens 406 and reducing lens 407. The light rays 420 from the intermediate image 430 are passed by the reducing lens 407 and the main objective system into a parallel viewing beam path 440.

In order to sharply adjust the system shown in FIG. 4 on the ocular fundus, the distance of the ophthalmic magnifier lens 406 from the main objective system 405 and the reducing lens 407 has to be reduced while the position of the ophthalmic magnifier lens 406 with respect to the cornea 501 of the patient eye 500 remains the same. This is explained now with respect to FIG. 5. The surgical microscope 402 is dropped in the direction of arrow 550. At the same time, the ophthalmic magnifier lens 406 is moved relative to the surgical microscope 402 in the direction of arrow 560.

Figure 5:
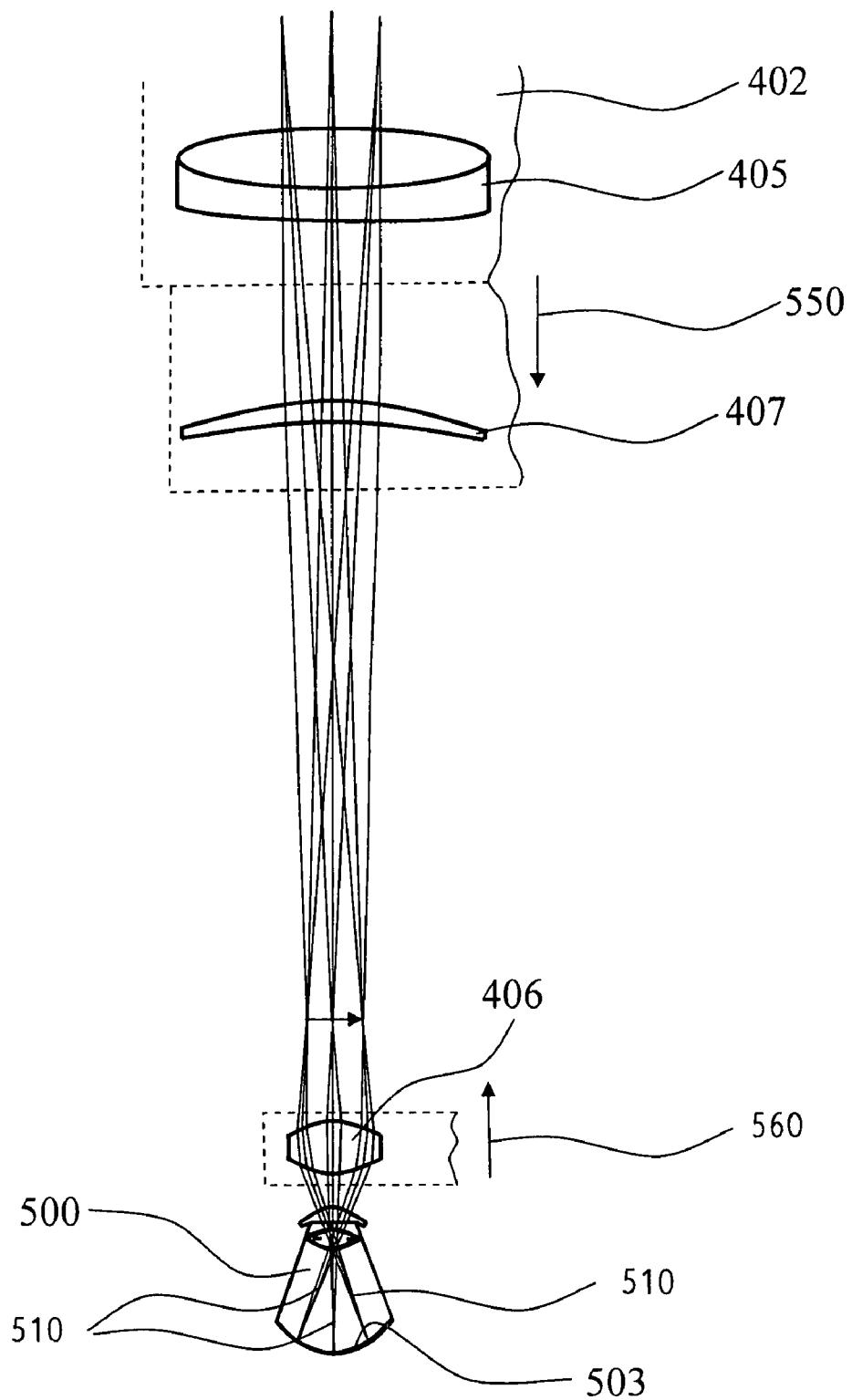
FIG. 5 is a schematic showing the section of the ophthalmic surgical microscope system wherein the apparatus pupil is adapted to the pupil of the patient eye being examined; and, FIG. 6 is a schematic of an ophthalmic surgical microscope system having an apparatus pupil which is not adapted to the pupil of the patient eye being examined.

The mutually matched movements of the surgical microscope 402 and the drive of the ophthalmic magnifier lens 406 is effected via the coupling 123 (FIG. 1) of the drive of the ophthalmic magnifier lens 116 with the drive 112 to adjust the surgical microscope 101. The mutually opposing movement of the surgical microscope 402 and the ophthalmic magnifier 406 perforce leads to an apparatus setting as shown in FIG. 5. This setting is optimal for the examination of the ocular fundus 503 of a patient eye 500 because here the viewing field is not limited by the pupil of the patient eye 500.

Preferably, in the ophthalmic surgical microscope system of the invention, a positioning control is provided for the drive 112 for the surgical microscope 101 of FIG. 1 and the drive 117 for the ophthalmic magnifier lens 116. The coupling of the drives (112, 117) is configured in correspondence to a nonlinear dependency which ensures that the position of the apparatus pupil is not changed when adjusting the surgical microscope 101 and ophthalmic ancillary module 114. Accordingly, during ophthalmic surgery on a patient eye, an always ideal adaptation of the apparatus pupil of the ophthalmic surgical microscope system to the pupil of the patient eye is ensured. With a coupling of this kind, a nonlinear relationship of the adjusting speed for the surgical microscope and the ophthalmic magnifier lens is present.

The coupling of the drives (112, 117) can, however, also be configured contradirectionally and in correspondence to a linear dependency. In this case, the positions of the apparatus pupils are changed but only insignificantly.

In that, in the surgical microscope system, a sensor is integrated for measuring the distance from the surgical microscope 101 of FIG. 1 to the patient eye 120, the favorable system setting to which the ophthalmic surgical microscope system should be set can be displayed to the operator by means of an adjustment indicator. In this way, unwanted movements of the patient eye during a surgical procedure can be compensated.

It is also possible to combine such a sensor with a control unit which ensures that the ophthalmic surgical microscope system automatically assumes the most favorable system setting when there is a movement of the patient eye.

Figure 6:
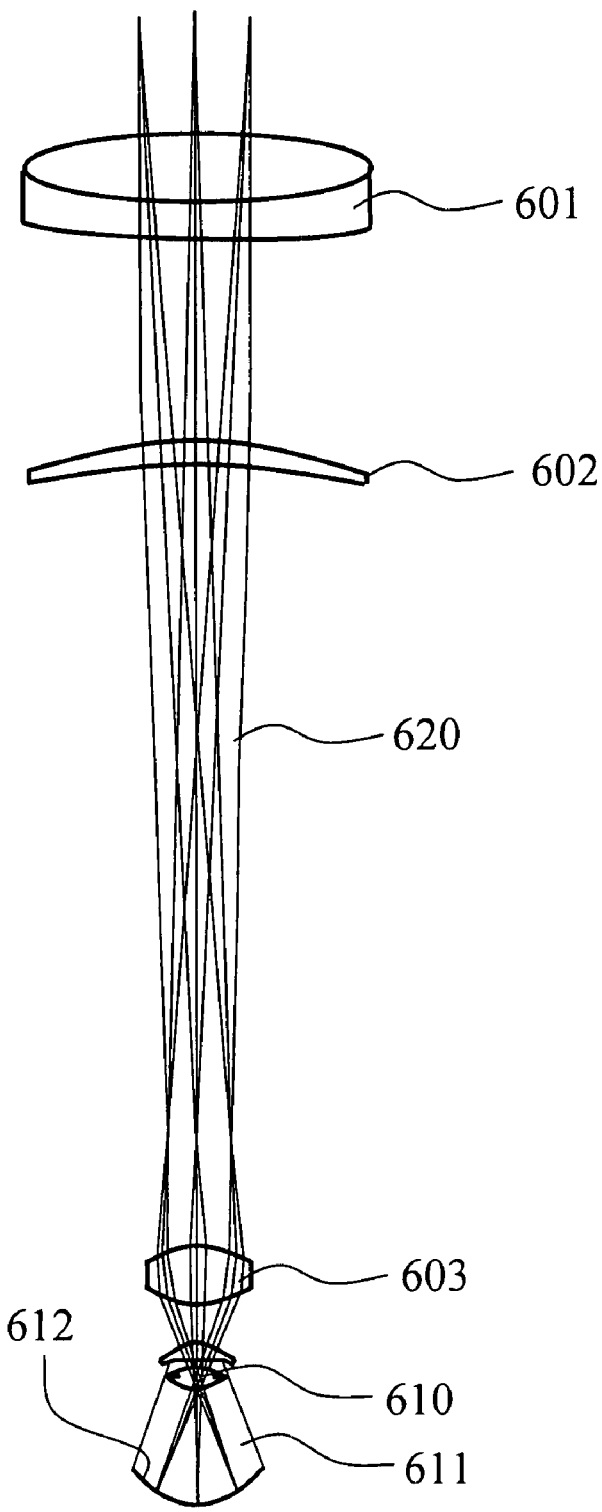

FIG. 6 shows a section of an ophthalmic surgical microscope system having a main objective system 601, reducing lens 602 and ophthalmic magnifier lens 603. The ophthalmic surgical microscope with a viewing beam path 620 permits a sharp imaging of the ocular fundus 612 of the patient eye. However, since the apparatus pupil of the system is not adapted to the pupil 610 of the patient eye 611, only a comparatively small portion of the ocular fundus 612 is imaged by the ophthalmic magnifier lens 603 in comparison to the setting of the ophthalmic surgical microscope system of the invention explained with respect to FIG. 5.

It is understood that the foregoing description is that of the preferred embodiments of the invention and that various changes and modifications may be made thereto without departing from the spirit and scope of the invention as defined in the appended claims.

What is claimed is:

1. An ophthalmic surgical microscope system defining viewing beam paths for viewing the eye of a patient, the ophthalmic surgical microscope system comprising:
   a surgical microscope;
   a carrier unit for accommodating said surgical microscope therein so as to be adjustable in elevation to adjust a first distance between said surgical microscope and the eye of the patient;
   a first drive for adjusting said surgical microscope in said elevation;
   an ophthalmic ancillary module including an adjustable ophthalmic magnifier lens displaceable for adjusting a second distance between said ophthalmic magnifier lens and said surgical microscope;
   a second drive for adjusting said ophthalmic magnifier lens;
   a drive coupling for coupling said first drive to said second drive; and,
   said drive coupling so coupling said first drive to said second drive that said surgical microscope and said ophthalmic magnifier lens are moved simultaneously in mutually opposite directions.

2. The ophthalmic surgical microscope system of claim 1, wherein said drive coupling so couples said first drive to said second drive that said surgical microscope and said ophthalmic magnifier lens are moved at approximately the same speed.

3. The ophthalmic surgical microscope system of claim 1, wherein said first drive is configured as a motorized drive.

4. The ophthalmic surgical microscope system of claim 3, wherein said second drive is configured as a motorized drive.

5. The ophthalmic surgical microscope system of claim 4, wherein said drive coupling is configured as an electronic coupling.

6. The ophthalmic surgical microscope system of claim 1, wherein said ophthalmic ancillary module includes a reducing lens system.

7. The ophthalmic surgical microscope system of claim 1, further comprising a system for beam transposition and image reversion.

8. The ophthalmic surgical microscope system of claim 1, further comprising pivot means for pivoting said ophthalmic ancillary module into and out of said viewing beam paths.

9. An ophthalmic surgical microscope system defining viewing beam paths for viewing the eye of a patient, the ophthalmic surgical microscope system comprising:
   a surgical microscope;
   a carrier unit for accommodating said surgical microscope therein so as to be adjustable in elevation to adjust a first distance between said surgical microscope and the eye of the patient;
   a first drive for adjusting said surgical microscope in said elevation;
   an ophthalmic ancillary module including an adjustable ophthalmic magnifier lens displaceable for adjusting a second distance between said ophthalmic magnifier lens and said surgical microscope;
   a second drive for adjusting said ophthalmic magnifier lens;
   a drive coupling for coupling said first drive to said second drive;
   said drive coupling so coupling said first drive to said second drive that said surgical microscope and said ophthalmic magnifier lens are moved simultaneously in mutually opposite directions; and,
   said drive coupling so coupling said first drive to said second drive that apparatus pupils of a system comprising said surgical microscope and said ophthalmic magnifier lens are fixed in space.

10. An ophthalmic surgical microscope system defining viewing beam paths for viewing the eye of a patient, the ophthalmic surgical microscope system comprising:
    a surgical microscope;
    a carrier unit for accommodating said surgical microscope therein so as to be adjustable in elevation to adjust a first distance between said surgical microscope and the eye of the patient;
    a first drive for adjusting said surgical microscope in said elevation;
    an ophthalmic ancillary module including an adjustable ophthalmic magnifier lens displaceable for adjusting a second distance between said ophthalmic magnifier lens and said surgical microscope;
    a second drive for adjusting said ophthalmic magnifier lens;
    a drive coupling for coupling said first drive to said second drive; and,
    said drive coupling so coupling said first drive to said second drive that said surgical microscope and said ophthalmic magnifier lens are moved simultaneously in mutually opposite directions in mutually matched movements so as to cause said ophthalmic magnifier lens to remain at a constant spacing relative to said eye of said patient.

11. The ophthalmic surgical microscope system of claim 10, wherein said drive coupling so couples said first drive to said second drive that apparatus pupils of a system comprising said surgical microscope and said ophthalmic magnifier lens are fixed in space.

* * * * *